United States Patent [19]

Degen et al.

[11] Patent Number: 5,068,385
[45] Date of Patent: Nov. 26, 1991

[54] PROCESS FOR THE PREPARATION OF ALKYL HALOGENOSILANES

[75] Inventors: Bruno Degen, Much; Kurt Feldner; Elke Licht, both of Leverkusen; Gebhard Wagner, Odenthal, all of Fed. Rep. of Germany

[73] Assignee: Bayer Aktiengesellschaft, Leverkusen, Fed. Rep. of Germany

[21] Appl. No.: 570,089

[22] Filed: Aug. 20, 1990

[30] Foreign Application Priority Data

Sep. 8, 1989 [DE] Fed. Rep. of Germany ....... 3929865

[51] Int. Cl.$^5$ ................................................ C07F 7/16
[52] U.S. Cl. .................................................... 556/472
[58] Field of Search ........................................ 556/472

[56] References Cited

U.S. PATENT DOCUMENTS

| Re. 33,452 | 11/1990 | Ward, III et al. | 556/472 |
|---|---|---|---|
| 2,889,350 | 6/1959 | Horny et al. | 556/472 |
| 3,057,894 | 10/1962 | Robinson | 556/472 X |
| 4,218,387 | 8/1980 | Maas et al. | 556/472 |
| 4,602,101 | 7/1986 | Hahn et al. | 556/472 |
| 4,656,301 | 4/1987 | Prud'Homme et al. | 556/472 |
| 4,898,960 | 2/1990 | Dosaj et al. | 556/472 |
| 4,946,978 | 8/1990 | Hahn et al. | 556/472 |
| 4,965,388 | 10/1990 | Hahn et al. | 556/472 |
| 4,973,725 | 11/1990 | Lewis et al. | 556/472 |

FOREIGN PATENT DOCUMENTS 1165026 3/1964 Fed. Rep. of Germany ...... 556/472

*Primary Examiner*—Paul F. Shaver
*Attorney, Agent, or Firm*—Sprung, Horn, Kramer & Woods

[57] ABSTRACT

A process for the preparation of alkyl halogenosilanes comprising reacting silicon with alkyl halide in the presence of a copper catalyst and promoter substances and phosphorous and phosphorous compounds in combination with indium or indium compounds or aluminum or aluminum compounds or a mixture of aluminum or aluminum compounds and indium or indium compounds.

4 Claims, No Drawings

PROCESS FOR THE PREPARATION OF ALKYL HALOGENOSILANES

This invention relates to a process for the preparation of alkyl halogenosilanes by the reaction of silicon with an alkyl halide in the presence of a copper catalyst. The invention relates in particular to a process for the preparation of methyl chlorosilanes in which phosphorus or phosphorus compounds in combination with copper alloys of the formula $Cu_xM_y$ (M = Al and/or In) or other suitable sources of the elements Al and In are used as promoters.

The basic process for the preparation of methyl chlorosilanes consists of the direct reaction of ground silicon with methyl chloride in the presence of copper as catalyst. The reaction is known to the artisan as the "Rochow-Synthesis" and is described, for example, in U.S. No. 2,380,995.

This process results in a mixture of methyl chlorosilanes in which dimethyldichlorosilane forms the main component. Methyl trichlorosilane and other methyl chlorosilanes are also formed, e.g. trimethylchlorosilane, methyl hydrogen dichlorosilane and higher boiling methyl chlorodisilanes.

Since the development of this method of synthesis, much work has been carried out concerned with improving this process and increasing the proportion of dimethyldichlorosilane, i.e. with the aim of rendering this synthesis as selective as possible for the formation of dimethyldichlorosilane. This is achieved mainly by observing the criteria for purity of the raw materials and by the judicious use of promoters. The use of promoters has been the main concern of some works carried out very recently, examples of which are given below: DE-A 3 425 424, EP-A 138 678, EP-A 138 679, DE.A 3 501 085, EP-A 191 502, EP-A 194 214, EP-A 195 728, EP.A 223 447 and U.S. No. 4,762,940.

It was also an object of the present invention to render the process as selective as possible for the production of dimethyldichlorosilane. A measure of this selectivity is in most cases expressed in the literature in terms of the ratio of methyl trichlorosilane to dimethyldichlorosilane (T/D) but the object of the present invention goes beyond this in that it also aims to reduce the proportion of other by-products, e.g. trimethylchlorosilane and the higher boiling methylchlorodisilanes.

According to the present invention, this purpose is achieved by either adding phosphorus or solid phosphorus compounds, preferably copper phosphide of the formula $Cu_3P$, to the catalyst or mixing the methyl chloride with gaseous phosphorus compounds such as phosphorus trichloride and at the same time adding copper alloys $Cu_xM_y$ in which M = Al and/or In to the catalyst. The ratio of x to y is preferably from 10:1 to 1:1.

It has already been disclosed in DP-PS 1 165 026 that the course of the direct synthesis can be influenced by the elements phosphorus, arsenic, antimony, bismuth, indium, thallium and gallium. The preferred embodiment, namely doping of silicon by means of a sintering process, is very energy consuming and is no longer in accordance with the state of the art. A similar process is described in Russian Patent Specification No. 754 895 in which phosphorus is again subjected to a sintering process together with copper and silicon.

In React. Solids. Proc. Int. Symp. 10th, 1984, Part B (1985), pages 941 946, J.G.M. Becht et al., report that phosphorus catalyzes the diffusion of copper in silicon to form $Cu_3Si$. It would therefore seem obvious to add the required quantity of phosphorus to the silicon used as raw material for the process of preparation, as claimed in the two applications, EP-A 272 860 and EP-A 273 635.

It is much more elegant, however, to add the phosphorus in the form of gaseous phosphorus compounds to the stream of methyl chloride when carrying out the direct synthesis of methyl chlorosilanes. This process is simpler and much more flexible and enables the silane producer to be more independent of the quality of the silicon and therefore constitutes considerable technical advance.

EP-A 223 447 and U.S. No. 4,762,940 show that the promoter effect of phosphorus can be considerably enhanced by adding to the catalyst not only the usual zinc promoter but in addition a combination of phosphorus, a phosphide or a compound capable of forming a phosphide and tin or a tin compound or arsenic or an arsenic compound instead of tin or a tin compound.

Tin is a higher homologous element of silicon while arsenic is a higher homologous element of phosphorus. It was therefore all the more surprising and completely new to find that phosphorus used in combination with elements of the Third Main Group. in particular with aluminum and indium, produced a marked improvement both in the reactivity and in the yield of dimethyldichlorosilane, this improvement being in particular combined with the production of smaller quantities of methyl tri chlorosilane, trimethyl monochlorosilane and the unwanted methyl chlorodisilanes.

Although it is disclosed in DP-PS 1 165 026 that the dimethyldichlorosilane content increases with increasing indium content, our own comparison experiments have shown that the presence of indium greatly increases the proportion of methyl chlorodisilanes formed.

The use of aluminum has already been described in surveys given in the literature. e.g. by R.Voorhoeve in "Organohalosilanes: Precursors to Silicones", Elsevier Publishing Company, (1967), Amsterdam, Netherlands. Aluminum is one of the elements in which the results are interpreted unequivocally: Acceleration of the reaction is found to take place. DE-SO 3 501 085 claims a catalyst composition which is characterized particularly by the simultaneous presence of tin or tin compounds and aluminum or aluminum compounds.

The present invention relates to a process for the preparation of alkyl halosilanes from silicon and an alkyl halide in the presence of a copper catalyst and promoter substances, in particular a zinc promoter, characterized in that phosphorus or phosphorus compounds in combination with indium or indium compounds or with aluminum or aluminum compounds are used in addition.

In a preferred embodiment of the present invention, phosphorus is either added to methyl chloride in the form of gaseous phosphorus compounds or to the mixture of catalyst/promoter in the form of intermetallic phases such as $Cu_3P$.

Aluminum is used as a calculated increase in the aluminum content of the silicon or, preferably as an intermetallic phase bound to copper. The $Cu_9Al_4$ phase is particularly suitable for this purpose but elementary aluminum may also be used.

Indium is preferably used in the form of elementary indium or bound to copper in an intermetallic phase.

The catalyst/promoter systems used according to the present invention contain from 50–1000 ppm, preferably from 100.500 ppm of phosphorus calculated as the element and based on silicon, from 50–5000 ppm, preferably from 100–1000 ppm, of aluminum calculated as the element and based on silicon or, in addition to or instead of aluminum, from 30–500 ppm of indium, calculated as the element and based on silicon, in addition to the copper catalyst and the zinc promoter.

Application of the present invention is not limited to a particular technique for carrying out the process of direct synthesis. Thus the reaction may be carried out either continuously or discontinuously in a fluidized out either continuously or discontinuously in a fluidized bed, a stirrer bed or a solid bed.

The following Examples serve to illustrate the present invention in more detail but are by no means to be regarded as limiting the invention (percentages denote percentages by weight).

All the experiments described below were carried out in a stirrer bed reactor of glass having an internal diameter of 30 mm and equipped with a spiral stirrer. The same quantity of silicon having the same particle size distribution of from 71 to 160 μm was used in each case.

Methyl chloride was passed through the catalyst mass from below through a glass frit at a pressure of 2 bar. The quantity of methyl chloride was kept constant at about 1.8 l/h at 2 bar in all cases. After the reaction mixture had been heated up and the reaction had started, the system was adjusted to a stationary experimental phase at 300° C. and the quantity and composition of crude silane mixture formed per unit time under these predetermined conditions were determined. The values given are in all cases average values obtained from four individual determinations under constant marginal conditions of 2 bar 1.8 l/h of methyl chloride and 300° C.

The catalyst mass consisted of 40 g of silicon containing the following impurities: 0.34% of iron, 0.17% of aluminum, 0.15% of calcium, 0.04% of titanium and 0.005% of phosphorus;

3.2 g of copper catalyst (partially oxidized Cu) and 0.05 g of ZnO.

According to the present invention, the other promoter additives were added to this basic mixtures, which was always kept constant, and the whole mixture was homogenized before use.

EXAMPLE 1

Example 1 demonstrates the effect of phosphorus/indium combinations:

|  |  | Experiment 1 |  | Experiment 2 |
|---|---|---|---|---|
| Silicon: |  | 40 g |  | 40 g |
| Catalyst: |  | 3.2 g |  | 3.2 g |
| Zinc oxide: |  | 0.05 g |  | 0.05 g |
| Indium: | metal | 0.004 g | $Cu_3In$ | 0.0133 g |
|  | (corresponds to 100 ppm) |  |  | (corresponds to 125 ppm) |
| Phosphorus: | $Cu_3P$ | 0.056 g | $Cu_3P$ | 0.028 g |
|  | (corresponds to 200 ppm) |  |  | (corresponds to 100 ppm) |
| Results: | Production rate (g/h) | Mono (%)* | Tri/Di | PS (%)** |
| Experiment 1 | 6.0 | 1.7 | 0.017 | 3.7 |
| Experiment 2 | 7.3 | 1.6 | 0.017 | 3.5 |

Mono: Trimethyl monochlorosilane
Tri/Di: Methyl trichlorosilane/dimethyldichlorosilane
PS: Polysilanes, in particular disilanes
*: % by wt. based on monomeric silanes
**: % by wt. based on total crude silane mixture

EXAMPLE 2

Example 2 demonstrates the effect of phosphorus/aluminum combinations:

|  |  | Experiment 3 |  | Experiment 4 |
|---|---|---|---|---|
| Silicon: |  | 40 g |  | 40 g |
| Catalyst: |  | 3.2 g |  | 3.2 g |
| Zinc oxide: |  | 0.05 g |  | 0.05 g |
| Aluminum: | Cu/Al 80/20 | 0.0212 g | $Cu_9Al_4$ | 0.0212 g |
|  | (corresponds to 100 ppm) |  |  | (corresponds to 84 ppm) |
| Phosphorus: | $Cu_3P$ | 0.056 g | $Cu_3P$ | 0.028 g |
|  | (corresponds to 200 ppm) |  |  | (corresponds to 100 ppm) |
| Results: | Production rate (g/h) | Mono (%)* | Tri/Di | PS (%)** |
| Experiment 3 | 5.50 | 1.3 | 0.020 | 2.6 |
| Experiment 4 | 6.75 | 1.4 | 0.039 | 2.2 |

EXAMPLE 3

Example 3 gives comparison experiments in each of which one element of the combination is missing:

|  | Experiment 5 | Experiment 6 | Experiment 7 |
|---|---|---|---|
| Silicon: | 40 g | 40 g | 40 g |
| Catalyst: | 3.2 g | 3.2 g | 3.2 g |
| Zinc oxide: | 0.05 g | 0.05 g | 0.05 g |
| Aluminum: | — | $Cu_9Al_4$ 0.0212 g (corresponds to 84 ppm) | — |
| Indium: | metal 0.004 g (corresponds to 100 ppm) | — | — |
| Phosphorus: | — | — | $Cu_3P$ 0.056 g (corresponds to 200 ppm) |
| Results: | Production rate (g/h) | Mono (%)* | Tri/Di | PS (%)** |
| Experiment 5 | 6.50 | 3.5 | 0.039 | 6.0 |
| Experiment 6 | 7.90 | 1.8 | 0.056 | 2.7 |
| Experiment 7 | 5.40 | 2.3 | 0.027 | 3.0 |

Example 3 shows that when the individual elements are used separately as promoters, it is not possible to achieve the optimum of all the assessed factors at the same time, namely production rate, Mono content, Tri/Di ratio and Proportion of high boiling components in the crude silane.

EXAMPLE 4

| Experiment 8 |  |  |  |
|---|---|---|---|
| Silicon |  | 40 g |  |
| Catalyst |  | 3.2 g |  |
| Zinc oxide |  | 0.05 g |  |
| Aluminum | $Cu_9Al_4$ | 0.0212 g | (corresponds to 84 ppm) |
| Indium | $Cu_3In$ | 0.0133 g | (corresponds to 125 ppm) |
| Phosphorus | $Cu_3P$ | 0.028 g | (corresponds to 100 ppm) |

-continued

| | Experiment 8 | | | |
|---|---|---|---|---|
| Results: | Production rate (g/h) | Mono (%)* | Tri/Di | PS (%)** |
| Experiment 8 | 6.53 | 1.65 | 0.038 | 4.8 |

What is claimed is:

1. A process for the preparation of alkyl halogenosilanes comprising reacting silicon with an alkyl halide in the presence of a copper catalyst and promoter substances and phosphorus and phosphorus compounds in combination with indium or indium compounds or aluminum or aluminum compounds or a mixture of aluminum or aluminum compounds and indium or indium compounds.

2. A process according to claim 1, wherein the promoter substances are zinc or zinc compounds.

3. A process according to claim 1, wherein phosphorus is added to the alkyl halide in the form of gaseous compounds.

4. A process according to claim 1, wherein the indium or aluminum is in the form of intermetallic phases bound to copper.

* * * * *